United States Patent [19]

Akasaki et al.

[11] Patent Number: 5,075,487
[45] Date of Patent: Dec. 24, 1991

[54] FLUORENE DERIVATIVE

[75] Inventors: Yutaka Akasaki; Katsuhiro Sato; Katsumi Nukada, all of Kanagawa, Japan

[73] Assignee: Fuji Xerox Co., Ltd., Tokyo, Japan

[21] Appl. No.: 506,602

[22] Filed: Apr. 10, 1990

Related U.S. Application Data

[63] Continuation-in-part of Ser. No. 436,875, Nov. 15, 1989, Pat. No. 5,011,757.

[30] Foreign Application Priority Data

Apr. 10, 1989 [JP] Japan ................................. 1-87860

[51] Int. Cl.⁵ ............................................ C07C 255/50
[52] U.S. Cl. ..................................... 558/402; 558/405
[58] Field of Search ................................. 558/402, 405

[56] References Cited

U.S. PATENT DOCUMENTS 5,011,969  4/1991  Akasaki et al. ..................... 558/402

Primary Examiner—Johann Richter
Attorney, Agent, or Firm—Finnegan, Henderson, Farabow, Garrett and Dunner

[57] ABSTRACT

A fluorene derivative useful as an electron transport material is disclosed, which is represented by formula (I)

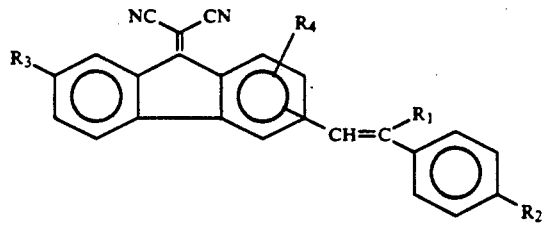

wherein $R_1$ represents a hydrogen atom or a phenyl group, $R_2$ represents a hydrogen atom, a nitro group, or an alkoxycarbonyl group, and $R_3$ and $R_4$ each represents a hydrogen atom or an alkyl group.

3 Claims, No Drawings

FLUORENE DERIVATIVE

CROSS-REFERENCE TO RELATED APPLICATION

This is a continuation-in-part-application of Ser. No. 436,875 filed Nov. 15, 1989 now U.S. Pat. No. 5,011,757.

FIELD OF THE INVENTION

The present invention relates to a novel fluorene derivative useful in an electrophotosensitive material.

BACKGROUND OF THE INVENTION

Electrophotographic photoreceptors employing organic photoconductive materials have conventionally been produced by forming a function-separated type photosensitive layer having a multilayer construction composed of a charge generating layer containing a charge generating material that absorbs visible light to generate charges and a charge transport layer containing a charge transport material that transports the charges. As charge transport materials, various substances having the property of transporting positive holes are known, such as amine compounds, hydrazone compounds, pyrazoline compounds, oxadiazole compounds, stilbene compounds, and carbazole compounds.

In such a function-separated type of electrophotographic photoreceptor, the mechanically strong charge transport layer generally constitutes the upper layer and, hence, where a conventional positive hole transport material is used for the charge transport layer, the photoreceptor is of the negatively charged type. However, preferred are positively charged photoreceptors from the standpoints of preventing ozone generation in corotrons and controlling the electrification of toners in developers. Although an electron transport material is required for making an electrophotographic photoreceptor to be of the positively charged type with the charge transport layer as the upper layer, a sufficiently effective electron transport material has not been known hitherto.

SUMMARY OF THE INVENTION

An object of the present invention is to provide an organic material useful as an electron transport material in multilayered electrophotographic photoreceptors of positively charged type.

The present invention have synthesized various compounds and studied their electrophotographic properties. As a result, it has now been found that certain fluorene derivatives function as excellent electron transport materials. The present invention has been completed base on this finding.

That is, the present invention provides a fluorene derivative represented by formula (I)

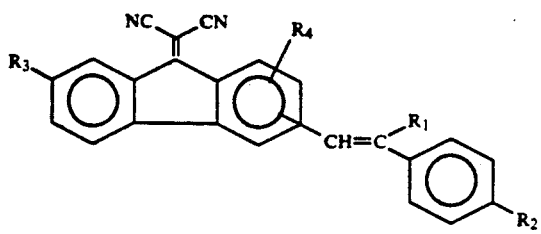

wherein $R_1$ represents a hydrogen atom or a phenyl group, $R_2$ represents a hydrogen atom, a nitro group, or an alkoxycarbonyl group, and $R_3$ and $R_4$ each represents a hydrogen atom or an alkyl group.

DETAILED DESCRIPTION OF THE INVENTION

In formula (I), the phenyl group for $R_1$ may be substituted or unsubstituted. Examples of the substituent include an alkyl group such as methyl, ethyl and butyl, and an alkoxycarbonyl group such as methoxycarbonyl, ethoxycarbonyl and butoxycarbonyl. The substituent is preferably bonded at the p-position of the phenyl group. The alkoxycarbonyl group for $R_2$ preferably has 2 to 9 carbon atoms and more preferably 3 to 9 carbon atoms. The alkyl group for $R_3$ and $R_4$ preferably has 1 to 8 carbon atoms and more preferably 1 to 4 carbon atoms.

Preferred are the fluorene derivatives having the group of

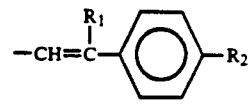

at the 2- or 4-position in the fluorene moiety.

As illustrated by the following reaction scheme, the fluorene derivative of this invention can be produced by oxidizing a fluorene derivative represented by formula (II) in a solvent such as a basic solvent (e.g., pyridine and quinoline) under oxygen atmosphere (e.g., air) at room temperature to 150° C. generally in the presence of a base catalyst such as hydroxides (e.g., NaOH) and benzyltrimethyl ammonium to thereby synthesize a fluorenone derivative represented by formula (III), and then refluxing the fluorenone derivative of formula (III), with heating, together with malononitrile in a solvent (e.g., pyridine and quinoline), or reacting the fluorenone derivative of formula (III) with malononitrile in methylene chloride or chloroform at −20° to 50° C. in the presence of titanium tetrachloride.

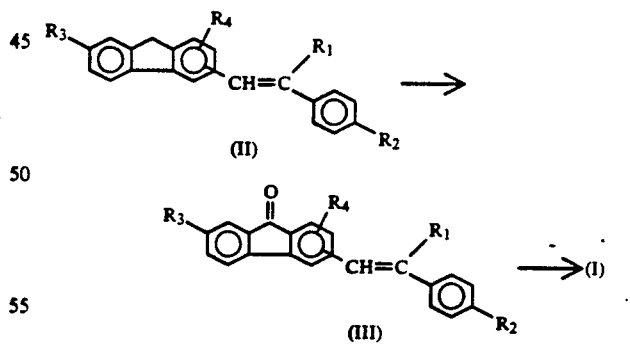

wherein $R_1$ to $R_4$ each is the same as defined above.

The fluorene derivative of formula (II) used in the above process can be synthesized by a method in which formylfluorene is reacted, for example, with diethyl diphenylphosphonate or a method in which chloromethylfluorene is reacted with triphenylphosphine and the resulting fluorene compound is then condensed with benzaldehyde or derivatives thereof. There reactions are generally carried out at −20 to 100° C. in a solvent such as ethanol, pyridine, dimethyl sulfoxide and ethersof ethylene glycol (e.g., ethylene glycol dimethyl ether) in the presence of base such as n-butyl litium, sodium hydroxide and sodium ethoxide.

A electrophotographic photoreceptor in which the fluorene derivative of formula (I) of the present invention can be used as an electron transport material comprises an electrically conductive substrate having a photosensitive layer formed thereon.

Examples of electrically conductive substrates which can be used in the present invention include metallic pipes, metallic plates, metallic sheets, metallic foils, highmolecular material films having electrical conductivity imparted thereto, high-molecular material films having a metallized layer such as a layer metallized with a metal such as Al, and high-molecular material films or paper coated with a metal oxide such as $SnO_2$ or a quaternary ammonium salt.

The photosensitive layer may be a single layer structure type or a laminated layer type wherein a charge generating layer and a charge transport layer are functionally separated from each other.

When the photosensitive layer is of a single layer structure type, the compound of formula (I) as a charge transport material may be incorporated in a binder resin layer containing a conventional charge generating agent. The single layer-type photosensitive layer may contain one or more compounds of formula (I) in an amount of 10 to 70 % by weight and preferably 20 to 60 % weight, and the thickness thereof is generally within the range of about 5 to about 30 μm.

When the photosensitive layer is of a laminated layer structure type, the charge generating layer may be formed by depositing a charge generating agent on the conductive substrate or by coatng the conductive substrate with a coating solution composed mainly of a charge generating agent and a binder resin.

Any single or mixture of conventional charge generating agents and any single or mixture of binder resins can be used. Examples of conventional charge generating agents include inorganic semiconductors such as trigonal selenium, organic semiconductors such as polyvinyl carbazole and organic pigments such as bis-azo compounds, tris-azo compounds, phthalocyanine compunds, pyrylium compounds and squarylium compounds. Examples of the binder resins include polystyrene, silicone resins, polycarbonate resins, acrylic resins, methacrylic resins, polyesters, vinyl polymers, celluloses and alkyd resins.

The thickness of the charge generating layer is generally within the range of about 0.05 to about 10 μm.

The change transport layer is formed on the charge generating layer. The charge transporting layer comprises one or more of the compounds of formula (I) and one or more of binder resins. The amount of the compound of formula (I) in the charge transporting layer is generally from 10 to 70 % by weight and preferably from 20 to 60 % by weight. This charge transport layer can be formed coating a coating solution composed mainly of the compound of formula (I), the binder resin and an appropriate solvent on the charge generating layer by means of an applicator, a bar coater, a dip coater or the like. The weight ratio of the compound of formula (I) and the binder resin is preferably in the range of from about 1/20 to about 20/1.

Any convertional binder resins can be used for the charge transport layer. Examples of binder resins include styrene-butadiene copolymer, vinyl-toluene-styrene copolymer, styrene-modified alkyd resin, silicone-modified alkyd resin, soybean oil-modified alkyd resin, vinylidene chloride-vinyl chloride copolymer, polyvinyl butyral, nitrated polystyrene, polymethylstyrene, polyisoprene, polyeter, phenolic resin, ketone resin, polyamide polycarbonate, polythiocarbonate, polyvinyl haloarylate, vinyl acetate resin, polystyrene, polyvinyl acrylate, polysulfone and polymethacrylate. If desired, electron-donating materials (positive hole transporting agents) such as tetraphenylbenzidine, triarylamines, hydrazone and stilbene may be added to the charge transport layer.

The thickness of the charge transport layer is generally within the range of about 2 to about 100 μm.

As described above, the compound of formula (I) is preferably used in a charge transport layer of function-separated type electrophotographic photoreceptor which is positively charged.

In the elctrophotographic photoreceptor of the present invention, a barrier layer may be optionally provided on the conductive substrate. The barrier-layer is effective in preventing undesired charge injection into the photosensitive layer from the substrate and thus is capable of improving the image quality. Suitable materials for the barrier layer include metal oxides such as aluminum oxide, acrylic resins, phenolic resins, polyester resins and polyurethane.

The present invention will be explained below in more detail by reference to the following Examples.

EXAMPLE 1

11.2 g of diethyl diphenylphosphonate and 300 ml of tetrahydrofurane (THF) were charged in a 500 ml three-necked flask, to which 23.2 mol of n-butyl litium was added, and subsequently a solution containing 7.1 g of 2-formylfluorene in 40 ml of THF was added dropwise over 30 minutes while cooling the reaction system with ice under nitrogen stream. The color of the reaction solution changed from yellow to green and then to brown. After stirring for 30 minutes, the resulting solution was heated under reflux over 2 hours and poured into 1 liter of water, to which 200 ml of hexane was further added. After filtration of the solution, an organic phase was separated from the resulting filtrate and dried with $Na_2SO_4$, followed by removing the solvent under reduced pressure. The residue was purified with a silica gel column chromatography (eluent: a mixture of methylene chloride/hexane (1/10 by weight)) and recrystallized from a mixture of ethyl acetate and ethanol, whereby 3.2 g (yield 25.3%) of light yellow crystals (m.p. 136.5°–138° C.) having the following structural formula was obtained.

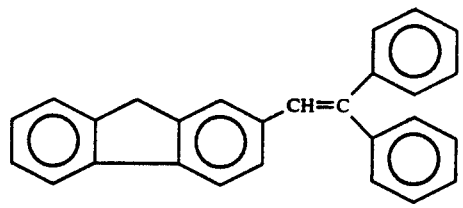

Into a 150 ml three-necked flask, 6.5 g of the thus obtained fluorene compound and 100 ml of pyridine were introduced. The mixture was cooled with ice and then 0.5 ml of a 40% methanol solution of benzyltrimethylammonium hydroxide was added thereto. The resulting mixture was stirred for one hour in an oxygen stream. After completion of the reaction, the contents were poured into 100 ml of water, resulting in a yellow precipitate. This precipitate was filtered off, washed with diluted hydrochloric acid and then with water, and dissolved in methylene chloride. This solution was dried with Na₂SO₄ and then purified with a silica gel short column (methylene chloride/hexane=1/1). Subsequently, the solvent was removed by evaporation under reduced pressure, and then the residue was recrystallized from a mixture of ethyl acetate and ethanol. Thus, 6.5 g (yield 94%) of a fluorenone compound having the following structural formula was obtained as orangish yellow needle crystals. The melting point of this compound was 172°-173.5° C.

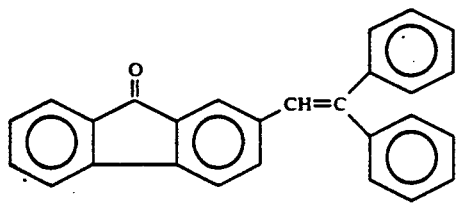

5.0 grams of this fluorenone derivative was placed, together with 90 ml of pyridine, in 250 ml three-necked flask, and the resulting mixture was heated at 100° C in a nitrogen stream, thereby dissolving the fluorenone derivative. Subsequently, a solution containing 1.8 g of malononitrile in 10 ml of pyridine was added dropwise to the above-obtained solution over about 10 minutes. After completion of the addition, the resulting mixture was refluxed for one hour and then cooled to room temperature. The reaction mixture was then poured into 100 ml of water, and the resulting precipitate was filtered off and washed with pyridine, diluted hydrochloric acid, water, and methanol in this order. Thus, 5.5 g (yield 97%) of a fluorene compound (Compound 1) having the following structural formula was obtained as a brown powder. The melting point of this compound was 293°-295.5° C.

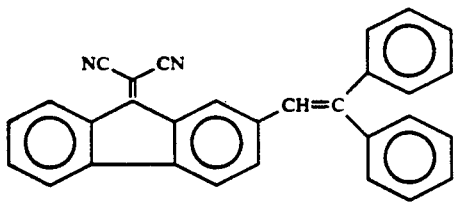

| Elementary Analysis: | | | |
|---|---|---|---|
| | C | H | N |
| Calculated: | 88.65 | 4.46 | 6.89 |
| Found | 88.75 | 4.29 | 6.76 |

Mass Spectrometric Analysis: M⁺ 406. UV Absorption Spectrum $\lambda_{max}$: 525 nm, 323 nm (in $CH_2Cl_2$) IR Absorption Spectrum: 2220 cm⁻¹ (KBr).

EXAMPLE 2

Into a 200 ml round-bottom flask, 5.0 g of a fluorene compound (m.p. 205.5°-207.5° C.) having the following structural formula

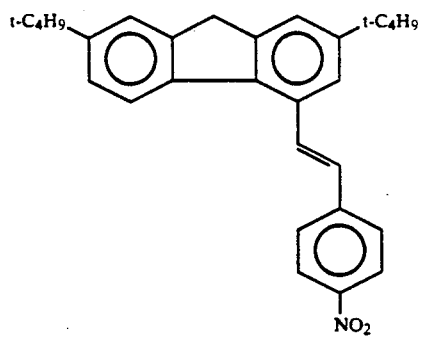

which had been obtained by reacting 2,7-di-t-butyl-4-chloromethylfluorene with triphenylphosphine and then condensing the reaction product with 4-nitrobenzaldehyde, was introduced together with 0.3 g of potassium hydroxide and 100 ml of pyridine. The resulting mixture was stirred at room temperature for 20 hours in an air atmosphere. After completion of the reaction, 200 ml of water was added to the reaction mixture, and the reaction product was extracted with methylene chloride. The resulting organic layer was dried with Na₂SO₄ and the solvent was then removed by evaporation under reduced pressure. The residue was purified with a silica gel short column (methylene chloride/hexane = 2/1). Thereafter, the solvent was removed by evaporation under reduced pressure and the residue was recrystallized from a mixture of ethyl acetate and ethanol, thereby obtaining 1.7 g (yield 33%) of a fluorenone compound having the following structural formula as a yellow powder. The melting point of this compound was 223°-224° C.

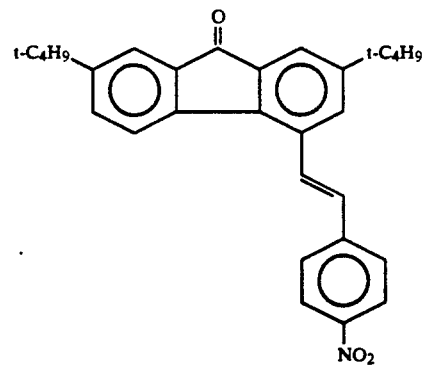

In 100 ml flask with a side arm were introduced 110 mg of the above-obtained fluorenone derivative, 0.33 g of malononitrile, and 50 ml of pyridine. The resulting mixture was refluxed for one hour in a nitrogen stream and the pyridine was then removed by evaporation under reduced pressure. The residue was dissolved in methylene chloride and purified with a silica gel short column (eluent: with methylene chloride). Subsequently, the methylene chloride was removed by evaporation under reduced pressure, and the residue was then washed with methanol and recrystallized from ethyl acetate. Thus, 0.84 g (yield 69%) of a fluorene compound (Compound 2) having the following structural formula was obtained as reddish brown needle crystals. The melting point of this compound was 289°-290° C.

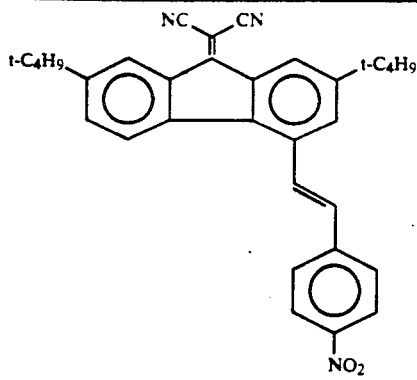

| Elementary Analysis: | | | |
|---|---|---|---|
| | C | H | N |
| Calculated: | 78.83 | 5.99 | 8.62 |
| Found: | 78.94 | 5.82 | 8.58 |

Mass Spectrometric Analysis: M+ 487. UV Absorption Spectrum $\lambda_{max}$: 366 nm, 259 nm (in $CH_2Cl_2$). IR Absorption Spectrum: 2224, 1594, 1528, 1344 $cm^{-1}$ (KBr).

EXAMPLE 3

A fluorene compound (m.p. 76°-77° C.) having the structural formula

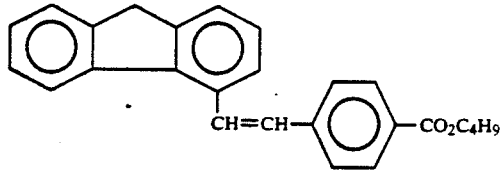

which had been synthesized by reacting 4-chloromethylfluorene with triphenylphosphine and then reacting the reaction product with butyl 4-formylbenzoate, was treated in the same manner as in Example 2. The resulting crude product was purified with a silica gel column (methylene chloride/hexane=½ to 1/0), thereby obtaining fluorenone compounds having the following structural formulae (cis form, melting point 96.5°-97.5° C. (yield 7.7%); trans form, melting point 116°-117.5° C. (yield 81.3 %)).

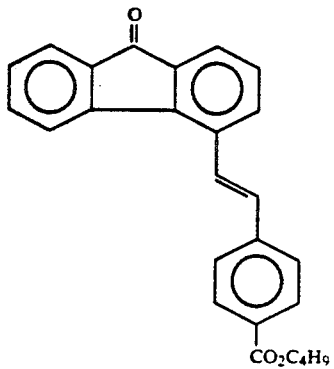

(1)

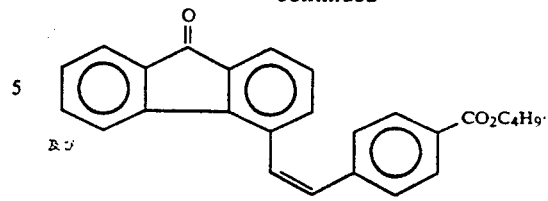

The trans-form fluorenone compound obtained above was treated in the same manner as in Example 2 to obtain a fluorene compound (Compound 3) having the following structural formula as reddish orange needle crystals (yield 77.6%). The melting point of this compound was 171-172° C.

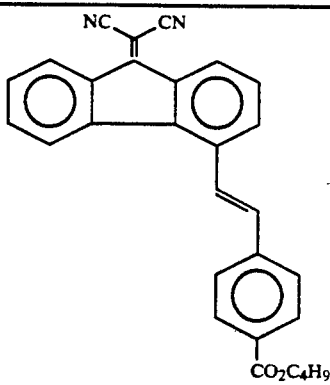

| Elementary Analysis: | | | |
|---|---|---|---|
| | C | H | N |
| Calculated: | 80.91 | 5.15 | 6.51 |
| Found: | 80.93 | 5.29 | 6.49 |

Mass Spectrometric Analysis: M+ 430. UV Absorption Spectrum $\lambda_{max}$: 345 nm, 316 nm, 267 nm. IR Absorption Spectrum: 2220, 1730, 1708 $cm^{-1}$ (KBr); 2224, 1712 $cm^{-1}$ ($CHCl_3$).

EXAMPLE 4

The cis-form fluorenone compound obtained in Example 3 was treated in the same manner as in Example 2 to obtain a fluorene compound (Compound 4) having the following structural formula as an orange powder (yield 81.2%). The melting point of this compound was 163°-165° C.

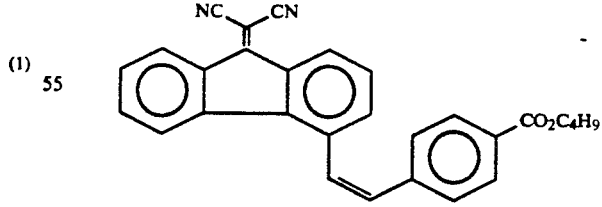

| Elementary Analysis: | | | |
|---|---|---|---|
| | C | H | N |
| Calculated: | 80.91 | 5.15 | 6.51 |
| Found: | 80.89 | 5.02 | 6.58 |

Mass Spectrometric Analysis: M+ 430. UV Absorption Spectrum $\lambda_{max}$: 358 nm, 297 nm, 286 nm, 270 nm. IR Absorption Spectrum: 2224, 1718 $cm^{-1}$ (KBr).

EXAMPLE 5

A fluorene compound (m.p. 67°-73° C.) having the structural formula

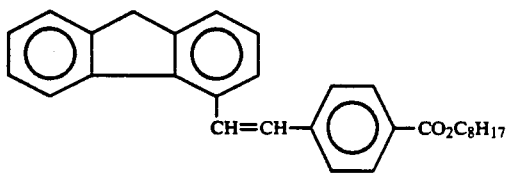

which had been synthesized by reacting a fluorene compound having the structural formula

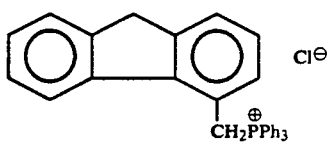

(wherein Ph represents a phenyl group) with octyl 4-formylbenzoate, was treated in the same manner as in Example 2. The resulting crude product was purified with a silica gel column (methylene chloride/hexane=½ to 1/0), thereby obtaining fluorenone compounds having the following structural formulae (cis form, melting point 81°-83° C. (yield 6.9%); trans form, melting point 113.5°-114.5° C. (yield 80.2%)).

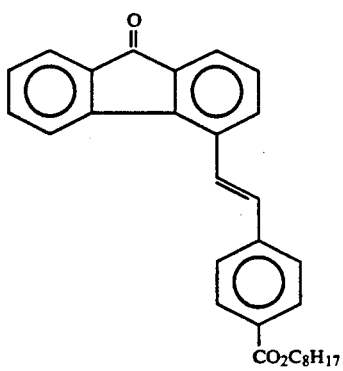

(2)

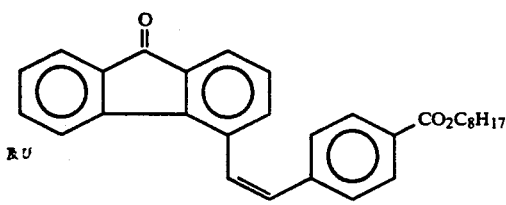

The trans-form fluorenone compound obtained above was treated in the same manner as in Example 2 to obtain a fluorene compound (Compound 5) having the following structural formula as reddish orange needle crystals (yield 82.0%). The melting point of this compound was 142°-144° C.

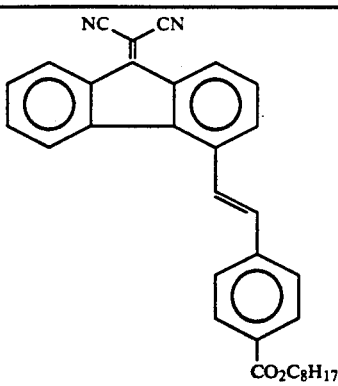

| Elementary Analysis: | | | |
|---|---|---|---|
| | C | H | N |
| Calculated: | 81.45 | 6.21 | 5.76 |
| Found: | 81.48 | 6.26 | 5.83 |

Mass Spectrometric Analysis: M+ 486. UV Absorption Spectrum $\lambda_{max}$: 345 nm, 315 nm, 265 nm. IR Absorption Spectrum: 2220, 1728, 1710 cm$^{-1}$ (KBr).

EXAMPLE 6

This cis-form fluorenone compound obtained in Example 5 was treated in the same manner as in Example 2 to obtain a fluorene compound (Compound 6) having the following structural formula as orange cotton-like crystals (yield 60.4%). The melting point of this compound was 120°-121.5° C.

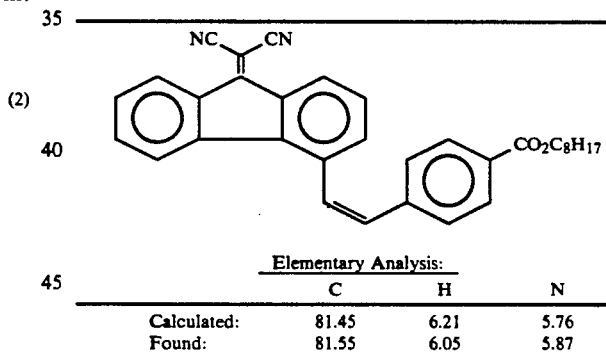

| Elementary Analysis: | | | |
|---|---|---|---|
| | C | H | N |
| Calculated: | 81.45 | 6.21 | 5.76 |
| Found: | 81.55 | 6.05 | 5.87 |

Mass Spectrometric Analysis: M+ 486. UV Absorption Spectrum $\lambda_{max}$: 355 nm, 297 nm, 285 nm, 270 nm. IR Absorption Spectrum: 2224, 1708 cm$^{-1}$ (KBr).

APPLICATION EXAMPLE 1

On an electrically conductive substrate was formed a charge generating layer (2.5 μm) composed of trigonal selenium/polyvinylcarbazole (trigonal selenium content: 7% by volume). Subsequently, a solution obtained by dissolving 0.5 g of Compound 3, 4, 5, or 6 and 0.75 g of a polycarbonate in 7 g of methylene chloride was coated on the charge generating layer at a wet thickness of 5 mils and then dried, thereby preparing an electrophotographic photoreceptor. Using an electrostatic copying-paper testing machine (SP428, manufactured by Kawaguchi Denki Seisakusho K.K., Japan), the electrophotographic photoreceptors obtained above were charged so as to have potentials of +800 V and −800 V and then exposed to white light at an illuminance of 5 luxes to measure the sensitivities (dV/dT) of the photoreceptors. The results obtained are shown in Table 1.

REFERENCE EXAMPLE

An electrophotographic photoreceptor was prepared in the same manner as in Application Example 1 except that 2,4,7-trinitrofluorene (TNF) as described in JP-B-49-31658 and JP-B-50-10496 was used in place of Compound 3. (The term "JP-B" used herein means Japanese patent publication.) The sensitivity of this photoreceptor was likewise measured, and the results obtained are shown in Table 1.

APPLICATION EXAMPLE 2

A 0.1 μm-thick charge generating layer was formed on an electrically conductive substrate by vapor deposition of metal-free phthalocyanine. On the other hand, 0.5 g of Compound 1 or 2 and 0.75 g of bisphenol A polycarbonate were dispersed in 1,2-dichloroethane and the dispersion was treated with a ball mill. The resulting dispersion was coated on the above-formed charge generating layer at a wet thickness of 7 mils and then dried to prepare an electrophotographic photoreceptor. The thus obtained electrophotographic photoreceptors were evaluated for sensitivity in the same manner as in Application Example 1 except that the photoreceptors were charged so as to have surface potentials of +500 V and −500 V. The results obtained are shown in Table 1.

TABLE 1

| | | Sensitivity (V/sec) | |
|---|---|---|---|
| | Compound | Positive charge | Negative charge |
| Application Example 1 | 3 | 190 | —* |
| | 4 | 90 | — |
| | 5 | 165 | — |
| | 6 | 86 | — |
| Reference Example | TNF | 66 | — |
| Application Example 2 | 1 | 70 | — |
| | 2 | 85 | — |

*Note. "—" means that the sample exhibited no sensitivity

The fluorene derivative represented by formula (I) of the present invention is superior in electron transport characteristics to TNF known as a relatively excellent material and, hence, it is useful as an electron transport material for use in electrophotographic photoreceptors. For example, an electrophotographic photoreceptor of the positively charged type having excellent electrophotographic properties can be produced by forming a charge generating layer on an electrically conductive support and then applying the fluorene derivative of this invention on the charge generating layer together with a film-forming resin to form a charge transport layer.

While the invention has been described in detail and with reference to specific embodiments thereof, it will be apparent to one skilled in the art that various changes and modifications can be made therein without departing from the spirit and scope thereof.

What is claimed is:

1. A fluorene derivative represented by formula (I)

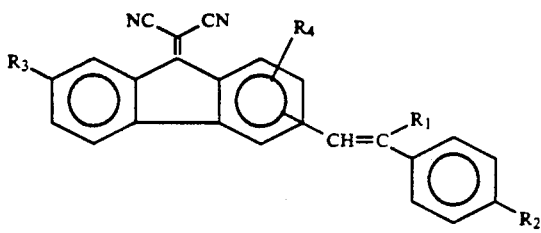

wherein $R_1$ represents a hydrogen atom or a phenyl group, $R_2$ represents a hydrogen atom, a nitro group, or an alkoxycarbonyl group, and $R_3$ and $R_4$ each represents a hydrogen atom or an alkyl group.

2. A fluorene derivative as in claim 1, wherein the alkoxycarbonyl group for $R_2$ has 2 to 9 carbon atoms, and the alkyl group for $R_3$ and $R_4$ has 1 to 8 caron atoms.

3. A fluorene derivative as in claim 2, wherein the group of

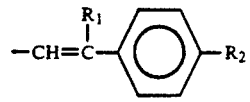

is bonded at 2- or 4- position of the fluorene nucleus.

* * * * *